United States Patent [19]

Krebs et al.

[11] 4,265,832

[45] May 5, 1981

[54] PREPARATION OF ANTHRANILAMIDES

[75] Inventors: Klaus-Werner Krebs; Carl Metzger, both of Dormagen, Fed. Rep. of Germany

[73] Assignee: Bayer Aktiengesellschaft, Leverkusen, Fed. Rep. of Germany

[21] Appl. No.: 83,882

[22] Filed: Oct. 11, 1979

Related U.S. Application Data

[63] Continuation of Ser. No. 895,316, Apr. 11, 1978, abandoned.

[30] Foreign Application Priority Data

Apr. 28, 1977 [DE] Fed. Rep. of Germany ....... 2719020

[51] Int. Cl.³ .......................................... C07C 102/00
[52] U.S. Cl. ............................... 564/163; 260/326.47; 546/226; 546/314
[58] Field of Search ...................... 260/558 A, 326.47; 546/226, 314

[56] References Cited

U.S. PATENT DOCUMENTS

| | | | |
|---|---|---|---|
| 4,032,571 | 6/1977 | Quadbeck-Seeger et al. | 260/558 A |
| 4,093,734 | 6/1978 | Krüger et al. | 260/558 A X |
| 4,191,706 | 3/1980 | Marquis et al. | 260/559 A |

FOREIGN PATENT DOCUMENTS 1543332   8/1969   Fed. Rep. of Germany .

OTHER PUBLICATIONS

Bunnett et al., J. Am. Chem. Soc. 88, (1966), No. 17, pp. 4001-4008.

*Primary Examiner*—Thomas A. Waltz
*Attorney, Agent, or Firm*—Sprung, Felfe, Horn, Lynch & Kramer

[57] ABSTRACT

A process for the preparation of an anthranilamide of the formula

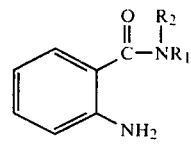

in which
 $R_1$ and $R_2$ each independently is hydrogen or $C_1$ to $C_4$ alkyl, or $R_1$ and $R_2$, together with the nitrogen atom to which they are bonded, form a heterocyclic ring,
comprising reacting isatoic anhydride of the formula

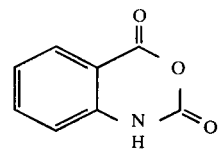

with an approximately equimolar amount of an amine of the formula

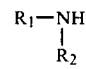

in water at a pH of about 7 to 10.5 and a temperature of about 20° to 100° C. Advantageously the reaction is effected in the presence of a buffer system comprising an amine of the formula

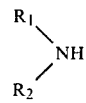

plus at least one of a hydrohalide and carbonic acid salt of such amine, e.g. ammonia or a lower alkyl amine plus the corresponding hydrochloride and/or carbonate.

3 Claims, No Drawings

PREPARATION OF ANTHRANILAMIDES

This is a continuation of application Ser. No. 895,316, filed Apr. 11, 1978, now abandoned.

The present invention relates to an unobvious process for the preparation of certain known anthranilamides, which can be used as organic intermediates, for example for insecticides, herbicides and dyestuffs.

It has already been disclosed that anthranilamides are obtained by reacting isatoic anhydride with amines in the uresence of inert organic solvents (DOS (German Published Specification) No. 1,543,332).

However, that process has a number of disadvantages. Thus, in order to isolate the anthranilamides, either large amounts of water must be added, which leads to a loss of the organic solvent employed, or the organic solvents must be separated off in a further process step, for example a distillation, after the reaction. A further disadvantage is that the anthranilamides prepared in the presence of inert organic solvents can be solvated, depending on the nature of the solvent, which, because of the adherence of the organic solvent, leads to difficulties during the filtration and drying of the desired products.

Furthermore, it has been disclosed that anthranilamides are obtained by reacting isatoic anhydride with amines in the presence of the corresponding amine hydrochlorides and with the addition of specific amounts of sodium chloride (J. Am. Chem. Soc. 88 (1966) No. 17, page 4,001).

However, the process described there cannot be transferred to an industrial scale. Thus, the reaction is carried out with, on the one hand, extremely high degrees of dilution, for example 0.001 molar solutions, and on the other hand with amine excesses and amine hydrochloride excesses, relative to isatoic anghydride, or more than 1 to 10. The recovery of such high amine exesses requires a considerable technical effort and expenditure of money. Furthermore, the addition of sodium chloride necessary to achieve satisfactory yields gives rise to an undesirably high chloride load in the effluent.

The present invention now provides a process for the preparation of an anthranilic acid amide of the general formula

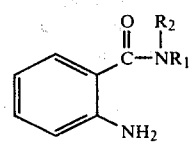

in which
R$_1$ and R$_2$, which may be identical or different, each denote hydrogen or a C$_1$ to C$_4$ alkyl group or R$_1$ and R$_2$, together with the nitrogen atom to which they are bonded, form a heterocyclic ring,
in which isatoic anhydride, of the formula

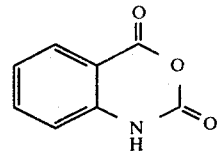

is reacted with an amine of the general formula

in which R$_1$ and R$_2$ have the meanings stated above, in a molar ratio of about 1:1 to 1.3 in water of a pH of about 7 to 10.15 and a temperature of about 20° to 100° C.

After isolating the anthranilic acid amines, the mother liquor frequently can be repeatedly recycled into the process at least twenty times.

Suitable agents for adjusting the pH values of 7 to 10.5 necessary for this process are all the known buffer systems of this range. However, those buffer systems which consist of mixtures of amine carbonates of the general formula

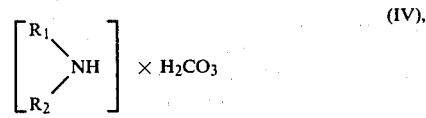

wherein R$_1$ and R$_2$ have the same meanings as in formula (III), and amines of the formula (III) are particularly advantageous. Buffer systems which are composed of amines of the formula (III) and amine carbonates of the formula (IV) and amine hydrohalides of the general formula

wherein
R$_1$ and R$_2$ have the same meanings as in formula (III) and
X is halogen, preferably chlorine, have also proved favorable.

It is decidodly surprising that, at molar ratios of isatoic anhydride to amine to about 1 to 1 and at concentrations of over 1 mol per liter, which are favourable for an industrial process, the anthranilic acid amides are obtained in high yield and purity if the reactions are carried out within the pH range according to the invention in the presence of buffer systems.

It has proved to be an additional advantage that the mother liquors from the procedure can be frequently recycled into the process, since the buffer system is also recycled with the mother liquor to the reaction of isatoic anhydride with amines.

Furthermore, it is particularly advantageous in this process that water is used exclusively as the solvent or dispersing agent and a working up of organic solvents is dispensed with.

The resulting anthranilamides are distinguished by surprisingly good ease of filtration coupled with good purity.

If isatoic anhydride and ammonia are used as starting materials, the course of the reaction can be represented by the following equation:

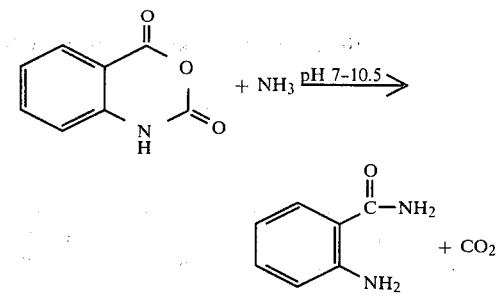

The isatoic anhydride used as a starting material is known. The same is true for the amines of the formula (III). There may be mentioned here, in particular: ammonia, methylamine, ethylamine, propylamine, butylamine, iso-propylamine, iso-butylamine, dimethylamine, diethylamine, dipropylamine, diisopropylamine, methylethylamine, methylpropylamine, methylisopropylamine, ethylpropylamine, ethylisopropylamine, piperidine, tetrahydropyridine and pyrrolidine.

Water is used exclusively as the diluent. The reaction is carried out at temperatures of from 20° to 100° C., preferably about 35° to 65° C.

In carrying out the process according to the invention, about 0.9 to 1.4 mols of amine and about 0.05 to 0.5 mol of amine carbonate as well as about 0.05 to 0.5 mol of amine hydrohalide (e.g. hydrochloride) are employed, for example, per mol of isatoic anhydride.

EXAMPLE 1a 1 mol of ammonia (76 ml of a 25% strength aqueous solution) together with 0.2 mol (19.2 g) of ammonium carbonate and 0.25 mol (10.8 g) of ammonium chloride were dissolved in 800 ml of water and the solution was warmed to 55° C. A pH value of 10.0 was set up in the solution. 1 mol (163 g) of isatoic anhydride was introduced incrementally into this solution over a period of 30 minutes, while stirring. After the addition of isatoic anhydride was complete, the mixture was warmed to 60° C. and stirred for a further 10 minutes. The solution now had a pH value of 7.8. On cooling to 0° C., the anthranilamide precipitated in the form of flaky crystals. The suspension was filtered over a suction filter. The solid was washed twice with 50 ml of ice-water and dried.

Yield: 123.8 g=91% of theory. Melting point: 110° C. Content (diazometrically): 99.6% of theory.

EXAMPLE 1b 1 mol of ammonia was added to the mother liquor from Experiment 1a, which has been separated off, and the pH was adjusted to 10 by adding 10.2 g (about 0.1 mol) of ammonium carbonate. 1 mol of isatoic anhydride was now introduced into the solution, warmed to 55° C., by the process described in Example 1 a and the mixture was worked up accordingly.

The yield of anthranilamide was 130.5 g=96% of theory. Melting point: 111° C. Content (diazometrically): 99.7% of theory.

The mother liquor obtained could be re-used for a further batch with the same result. A comparable result was obtained even after repeating the reaction 20 times, re-using, in each case, the mother liquor.

EXAMPLE 2 (COMPARISON EXAMPLE)

1.4 mols of ammonia (105 ml of a 25% strength aqueous solution) were initially introduced into 800 ml of water and the mixture was warmed to 55° C. The solution had a pH value of 12. 1 mol (163 g) of isatoic anhydride were continuously introduced into this solution over a period of 30 minutes, while stirring. After the addition of isatoic anhydride had ended, the mixture was subsequently stirred for a further 10 minutes at 60° C. The pH value of the solution was now 8.8. The reaction mixture was cooled to 0° C. and the anthranilamide which had precipitated was separated off over a suction filter and worked up according to the procedure in Example 1a.

Yield=106 g=77.9% of theory. Melting point: 109° C. Content (diazometrically): 99.4% of theory.

EXAMPLE 3

1.2 mols of isopropylamine (125 ml of a 70% strength aqueous solution, density 0.81), 0.2 ml of isopropylamine carbonate and 0.25 mol of isopropylamine hydrochloride were initially introduced into 1 liter of water. A pH value of 10.6 was set up in the solution. After warming the solution to 45° C., 1 mol (163 g) of isatoic anhydride was added over a period of 30 minutes. The pH value fell to 8.1 in the course of the reaction. At the same time, water-insoluble, colorless anthranilic acid isopropylamide precipitated. After the total amount of isatoic anhydride had been added, the mixture was heated to 60° C. and stirred for a further 10 minutes. After cooling to 10° C., the anthranilic acid isopropylamide was separated off over a suction filter, washed with ice-water and dried.

Yield: 146.4 g=82.2% of theory. Melting point: 146.0° C. Content: 98.8%=81.3% of theory.

14.2 g of a solid which melted at 176°–178° C., which was identified as N-(2-carboxyphenyl)-N'-isopropylurea, were isolated from the mother liquor by acidifying to pH 1. (Yield: 6.4%, relative to isatoic anhydride).

EXAMPLE 3a (COMPARISON EXAMPLE)

2 mols of isopropylamine (208.4 ml of a 70% strength aqueous solution, density 0.81) were initially introduced into 1 liter of water. A pH value of 12.35 was set up in the solution. After warming the solution to 45° C., 1 mol (163 g) of isatoic anhydride was introduced over a period of 30 minutes. The pH value fell to 9.2 in the course of the reaction. After the total amount of isatoic anhydride had been added, the mixture was heated to 60° C. and stirred for a further 10 minutes. After cooling to 10° C., the anthranilic acid isopropylamide was separated off over a suction filter, washed with ice-water and dried.

Yield: 107.6 g=60.4% of theory. Melting point: 145°–146° C. Content: 95.9%=57.9% of theory.

88 g of N-(2-carboxyphenyl)-N'-isopropylurea were isolated from the mother liquor by acidifying to pH 1. (Melting point: 176°–177° C: yield: 39.6%, relative to isatoic anhydride).

It will be appreciated that the instant specification and examples are set forth by way of illustration and not limitation, and that various modifications and changes may be made without departing from the spirit and scope of the present invention.

What we claim is:

1. A process for the preparation of anthranilamide of the formula

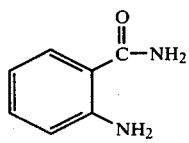

comprising reacting isatoic anhydride of the formula

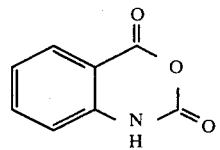

with an approximately equimolar amount of ammonia in a solvent consisting of water at a pH of about 7 to 10.5 and a temperature of about 20° to 100° C., and maintaining the pH with the aid of a buffer system comprising ammonia, an ammonium halide and carbonate, about 0.9 to 1.4 mols of ammonia, about 0.05 to 0.5 mol of the ammonium carbonate and about 0.05 to 0.5 mol of the ammonium halide being used per mol of isatoic anhydride.

2. A process according to claim 1, including the additional steps of recovering the anthranilamide from the reaction medium and recycling the residual reaction medium for use as solvent in further reaction.

3. A process according to claim 1, in which the reaction is effected at about 35° to 65° C.

* * * * *